US012599692B1

(12) United States Patent
Xia

(10) Patent No.: US 12,599,692 B1
(45) Date of Patent: Apr. 14, 2026

(54) VEHICLE-MOUNTED AROMATHERAPY DIFFUSER

(71) Applicant: Shenzhen Siweiyi Technology Co., Ltd., Shenzhen City (CN)

(72) Inventor: Xiaoli Xia, Ji'an City (CN)

(73) Assignee: Shenzhen Siweiyi Technology Co., Ltd., Shenzhen City (CN)

( * ) Notice: Subject to any disclaimer, the term of this patent is extended or adjusted under 35 U.S.C. 154(b) by 0 days.

(21) Appl. No.: 19/315,733

(22) Filed: Sep. 1, 2025

(30) Foreign Application Priority Data

Jul. 22, 2025 (CN) .......................... 202521536780.1

(51) Int. Cl.
*A61L 9/00* (2006.01)
*A61L 9/14* (2006.01)
*B05B 1/08* (2006.01)
*B65D 88/54* (2006.01)
*B67B 5/00* (2006.01)

(52) U.S. Cl.
CPC ..................................... *A61L 9/14* (2013.01)

(58) Field of Classification Search
CPC ......... A61L 9/14; A61L 2209/13; B05B 1/00; B67B 5/00; B65D 88/54; A61M 3/025; B60C 23/00; A24F 40/46
USPC ............ 422/5, 306; 128/200.11; 222/153.13, 222/321.1; 239/101, 589; 141/38
See application file for complete search history.

(56) References Cited

U.S. PATENT DOCUMENTS

| | | | | |
|---|---|---|---|---|
| 9,227,469 | B2 * | 1/2016 | Jhou | ...................... B60C 23/00 |
| 2005/0284474 | A1 * | 12/2005 | Tseng | ..................... A61M 11/06 |
| | | | | 128/203.12 |
| 2010/0084484 | A1 * | 4/2010 | Sevy | ................... A61M 11/001 |
| | | | | 239/340 |
| 2023/0355825 | A1 | 11/2023 | Long | |
| 2024/0165289 | A1 | 5/2024 | Long | |
| 2024/0207479 | A1 | 6/2024 | Long | |
| 2024/0207568 | A1 | 6/2024 | Chen | |
| 2024/0374861 | A1 | 11/2024 | Liu | |

* cited by examiner

*Primary Examiner* — Monzer R Chorbaji
(74) *Attorney, Agent, or Firm* — Ricky Lam

(57) ABSTRACT

Disclosed is a vehicle-mounted aromatherapy diffuser, including an aromatherapy body, wherein the aromatherapy body includes a first housing and an atomization mechanism, the atomization mechanism is mounted on the first housing, and the aromatherapy body is provided with a mounting groove; and an air pump body, wherein the air pump body is arranged in the mounting groove, the air pump body includes an air pump assembly, a second housing and a third housing, the second housing and the third housing are mutually buckled to form an mounting space, the air pump assembly is arranged in the mounting space and is communicated with the atomization mechanism, and the second housing is made of a flexible material. This ensures a stable connection between the air pump and the atomization mechanism while effectively buffering the vibration generated during the operation of the air pump assembly and reducing the rigid conduction path.

14 Claims, 5 Drawing Sheets

VEHICLE-MOUNTED AROMATHERAPY DIFFUSER

CROSS-REFERENCE TO RELATED APPLICATIONS

The application claims priority of Chinese patent application 202521536780.1, filed on Jul. 22, 2025, which is incorporated herein by reference in its entireties.

TECHNICAL FIELD

The present invention relates to the technical field of vehicle-mounted aromatherapy diffusers, and in particular, to a vehicle-mounted aromatherapy diffuser.

BACKGROUND

A vehicle-mounted aromatherapy diffuser, as a common device to improve the comfort of the driving environment, has a core function of atomizing aromatherapy essential oils through an air pump and diffusing the aromatherapy essential oils into the interior space of a vehicle. However, the air pump structure in the prior art generally has the problem of excessive noise during operation. Due to the relatively enclosed and confined interior space of a vehicle, mechanical vibrations and airflow noise are easily amplified, particularly during low-speed driving or idling conditions. The continuous low-frequency hum produced by the air pump compromises the cabin tranquility, impairs the auditory comfort of drivers and passengers, and even interferes with in-vehicle voice systems or call quality.

To meet the requirements of atomization efficiency, traditional air pumps often use high-speed motors or rigid pump body structures, which lack effective vibration and noise reduction designs, resulting in prominent mechanical friction noise and airflow whistling noise during operation. Therefore, the development of a vehicle-mounted aromatherapy diffuser that reduces operation noise has become a technical issue that needs to be urgently resolved in the prior art.

SUMMARY

A primary objective of the present invention is to provide a vehicle-mounted aromatherapy diffuser, which aims to improve the practicality of the vehicle-mounted aromatherapy diffuser.

To achieve the objective, the vehicle-mounted aromatherapy diffuser provided by the present invention includes:

an aromatherapy body, wherein the aromatherapy body includes a first housing and an atomization mechanism, the atomization mechanism is mounted on the first housing, and the aromatherapy body is provided with a mounting groove; and an air pump body, wherein the air pump body is arranged in the mounting groove, the air pump body includes an air pump assembly, a second housing and a third housing, the second housing and the third housing are mutually buckled to form an mounting space, the air pump assembly is arranged in the mounting space and is communicated with the atomization mechanism, and the second housing is made of a flexible material.

According to the technical solution of the present invention, the air pump assembly is encapsulated in the second housing made of a flexible material and is buckled to the third housing to form a closed mounting structure. This ensures a stable connection between the air pump and the atomization mechanism while effectively buffering the vibration generated during the operation of the air pump assembly and reducing the rigid conduction path. Meanwhile, the flexible second housing has a certain absorption and blocking effect on the air disturbance sound and mechanical noise generated by the air pump, and reduces the resonance and outward transmission of the sound in the first housing, which helps to achieve the shock absorption and noise reduction effect of the air pump assembly, thereby improving the quiet performance of the vehicle-mounted aromatherapy diffuser and enhancing the in-vehicle comfort experience.

BRIEF DESCRIPTION OF THE DRAWINGS

To more clearly illustrate the technical solutions in the embodiments of the present invention or in the prior art, the drawings required to be used in the description of the embodiments or the prior art are briefly introduced below. It is obvious that the drawings in the description below are only some embodiments of the present invention, and those of ordinary skill in the art can obtain other drawings according to structures illustrated in these drawings without creative efforts.

DESCRIPTIONS OF REFERENCE NUMERALS

Figure 1:
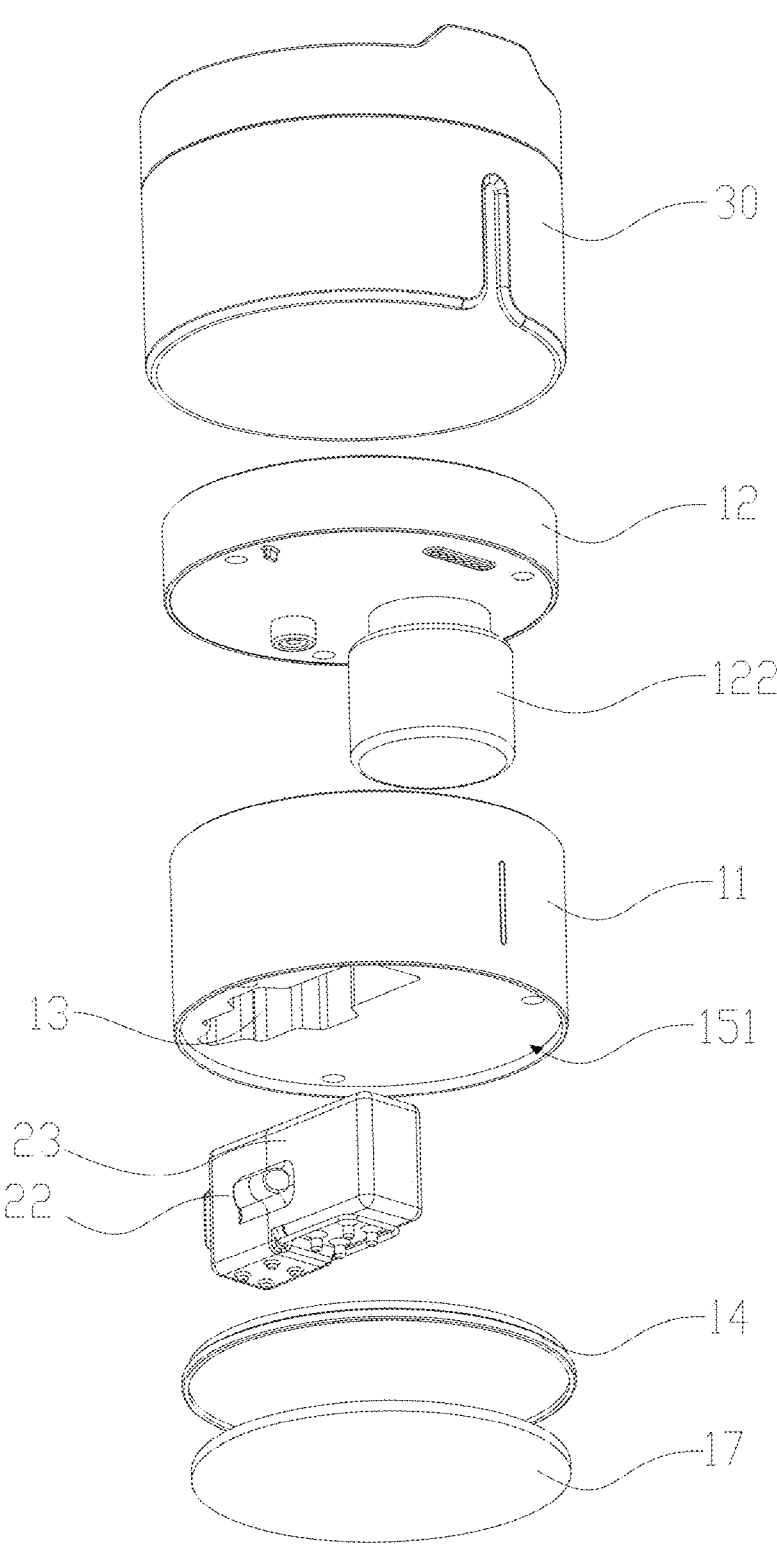
FIG. 1 is a schematic diagram of an exploded structure of a vehicle-mounted aromatherapy diffuser according to the present invention from one angle.

11. first housing; 12. atomization mechanism; 121. atomizer; 122. essential oil bottle; 123. air guide assembly; 124. air inlet; 13. mounting groove; 14. cover plate; 15. mounting base; 151. fixing groove; 161. main control board; 162. power supply seat; 163. power supply terminal; 17. anti-slip pad; 20. air pump body; 21. air pump assembly; 211. motor; 212. cylinder; 213. air outlet; 22. second housing; 221. air guide channel; 23. third housing; 24. mounting space; 25. fastening boss; 26. abutting protrusion; 27. electric terminal; 28. movable handle; and 30. mounting sleeve.

The realization of the objectives, the functional features, and the advantages of the present invention will be further explained in conjunction with the embodiments and with reference to the drawings.

DETAILED DESCRIPTION OF THE EMBODIMENTS

The technical solutions in the embodiments of the present invention will be clearly and completely described below with reference to the drawings in the embodiments of the present invention. It is apparent that the described embodiments are only some, but not all, embodiments of the present invention. Based on the embodiments of the present invention, all other embodiments obtained by those of ordinary skill in the art without creative efforts fall within the protection scope of the present invention.

It should be noted that, if directional indications (such as upper, lower, left, right, front and rear) are involved in the embodiments of the present invention, the directional indications are only used to explain the relative positional relationships, the motion situations and the like between individual components under a certain pose (as shown in the drawings), and if the certain pose is changed, the directional indications are changed accordingly.

In addition, if there are descriptions relating to "first", "second" and the like in the embodiments of the present invention, the descriptions of "first", "second" and the like are for descriptive purposes only and are not to be construed as indicating or implying relative importance thereof or implicitly indicating the quantities of the indicated technical features. Thus, a feature defined by "first" or "second" may explicitly or implicitly include at least one such feature. In addition, "and/or" appearing herein is meant to include three parallel solutions, and taking "A and/or B" as an example, it includes solution A, or solution B, or both solution A and solution B. In addition, the technical solutions among various embodiments may be combined with each other, however, this combination must be based on that it can be implemented by those of ordinary skill in the art. When the combination of the technical solutions is contradictory or cannot be implemented, such a combination of the technical solutions should not be considered to exist, and is not within the protection scope of the present invention.

The present invention provides a vehicle-mounted aromatherapy diffuser.

In an embodiment of the present invention, as shown in FIGS. 1 to 7, the vehicle-mounted aromatherapy diffuser includes an aromatherapy body and an air pump body 20, wherein the aromatherapy body includes a first housing 11 and an atomization mechanism 12 mounted on the first housing 11, and the air pump body 20 is detachably arranged in a mounting groove 13 provided in the aromatherapy body, which facilitates a user to replace the air pump body 20 and thereby extends the service life of the aromatherapy diffuser. A shape of the mounting groove 13 is adapted to a shape of the air pump body 20, so that rapid embedding of the air pump body 20 is achieved.

The first housing 11, as an external bearing structure of the aromatherapy diffuser, is configured to mount and protect other main components of the aromatherapy diffuser. The atomization mechanism 12 is arranged inside the first housing 11, and includes an atomizer 121, an essential oil bottle 122, and an air guide assembly 123 communicated with the atomizer 121. The air guide assembly 123 is configured to guide the airflow delivered by the air pump body 20 to the atomizer 121, and drive the atomizer 121 to atomize and diffuse the essential oil.

Further, the vehicle-mounted aromatherapy diffuser also includes a mounting sleeve 30, and the mounting sleeve 30 is sleeved on the aromatherapy body, thereby improving the mounting stability between the atomization mechanism 12 and the first housing 11, and further improving the practicality of the aromatherapy diffuser.

The air pump body 20 includes a second housing 22 and a third housing 23, which are mutually buckled by snap-fit or screws to form a closed mounting space 24 for accommodating the air pump assembly 21. The second housing 22 is made of a flexible material. This material can absorb and buffer the vibrations generated by the air pump assembly 21 during operation, thereby effectively suppressing the mechanical vibrations and low-frequency noise transmitted to the outside by a cylinder 212 during the operation of the air pump. The third housing 23 is a structural support component, and is configured to enhance the overall rigidity and define a position of the air pump assembly 21 together with the second housing 22.

The flexible material may be silicone, rubber, or the like. No specific limitation is made herein.

The air pump assembly 21 is arranged within the mounting space 24 formed by the second housing 22 and the third housing 23, and is communicated with the atomization mechanism 12 by the air guide assembly 123, so as to ensure a continuous and airtight airflow path. In addition, the second housing 22 forms a covering structure around the air pump assembly 21 through a flexible covering to further enhance vibration resistance.

Through the coordinated implementation of these structures, the aromatherapy diffuser effectively reduces the mechanical and airflow noise caused by the operation of the air pump in a vehicle environment while maintaining atomization efficiency. This aromatherapy diffuser is particularly suitable for in-vehicle spaces where a quiet environment is required, enhances driving comfort and user experience, and has excellent practicality and market value.

According to the technical solution of the present invention, the air pump assembly 21 is encapsulated in the second housing 22 made of a flexible material and is buckled to the third housing 23 to form a closed mounting structure. This ensures a stable connection between the air pump and the atomization mechanism 12 while effectively buffering the vibration generated during the operation of the air pump assembly 21 and reducing the rigid conduction path. Meanwhile, the flexible second housing 22 has a certain absorption and blocking effect on the air disturbance sound and mechanical noise generated by the air pump, and reduces the resonance and outward transmission of the sound in the first housing 11, which helps to achieve the shock absorption and noise reduction effect of the air pump assembly 21, thereby improving the quiet performance of the vehicle-mounted aromatherapy diffuser and enhancing the in-vehicle comfort experience.

Further, as shown in FIGS. 1 to 7, the air pump assembly 21 includes a motor 211 and a cylinder 212 fixed to the motor 211, the second housing 22 is arranged to cover the cylinder 212, the third housing 23 is arranged to cover the motor 211, and the cylinder 212 is communicated with the atomization mechanism 12. A radial length of the cylinder 212 is greater than a radial length of the motor 211. In this embodiment, the air pump assembly 21 is driven by the motor 211 and compresses and delivers air through the cylinder 212. The cylinder 212 is communicated with the atomization mechanism 12 through the air guide assembly 123 to form a stable air path. The second housing 22 is made of a flexible material and directly covers the outside of the cylinder 212, so as to absorb vibrations of the cylinder 212 during high-frequency operation. The third housing 23 is made of a rigid material and covers the outside of the motor 211, so as to enhance the structural strength of the first housing 11 and protect the motor 211. The cylinder 212 has a larger diameter than the motor 211, so that the vibration source is concentrated in an area covered by the flexible first housing 11, thereby further optimizing the vibration reduction effect. This structure considers both mechanical protection and noise suppression, and improves the quiet performance of the aromatherapy diffuser during operation.

Further, as shown in FIGS. 1 to 7, the third housing 23 is made of a hard material. In this embodiment, the third housing 23, as one of outer housings of the air pump body 20, is made of a rigid material such as acrylonitrile butadiene styrene (ABS) and polycarbonate (PC), and is configured to stably support the internal motor 211 to prevent the motor 211 from being displaced or shaken during operation. Meanwhile, the rigid material has good thermal stability and structural pressure resistance, which can improve the overall service life of the air pump. This design enhances the mechanical strength and assembly reliability of the air pump body 20.

Figure 4:
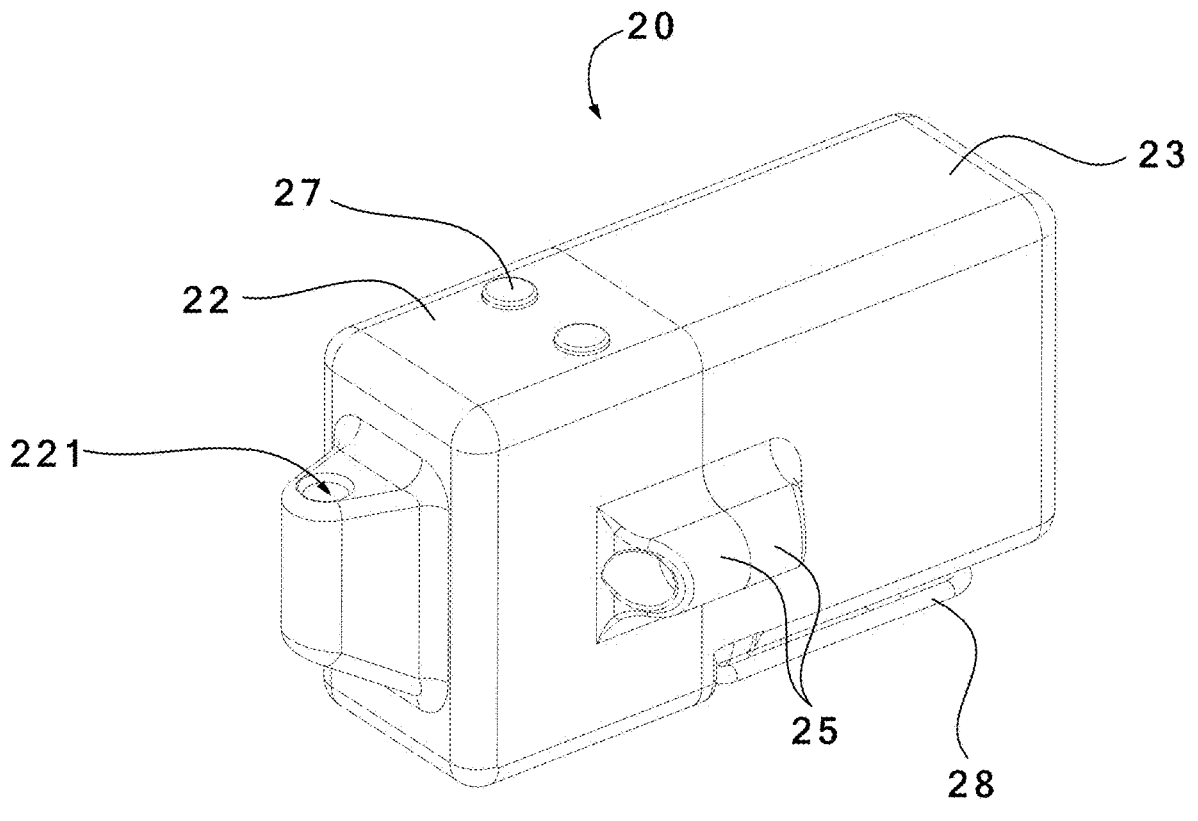
FIG. 4 is a schematic diagram of a structure of an air pump body from one angle.
Figure 5:
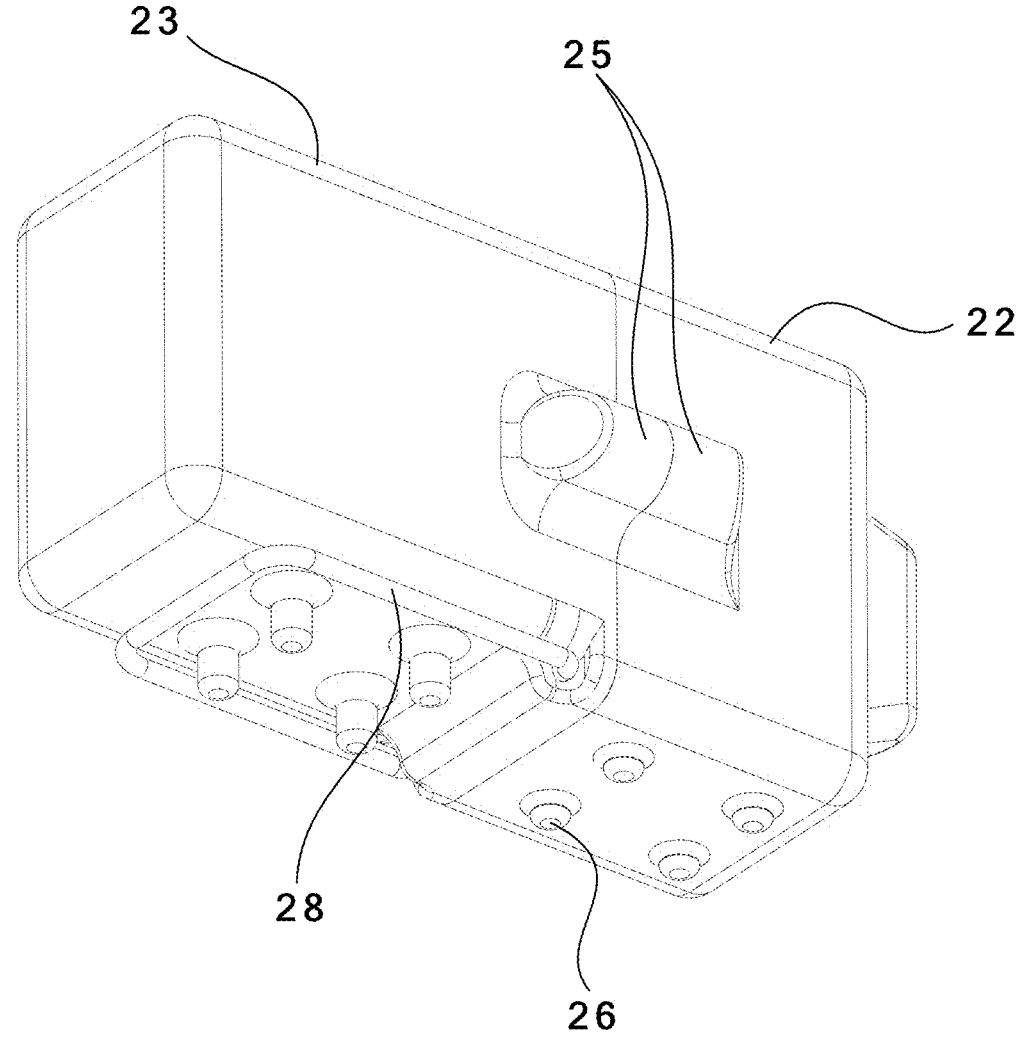
FIG. 5 is a schematic diagram of a structure of an air pump body from another angle.
Figure 6:
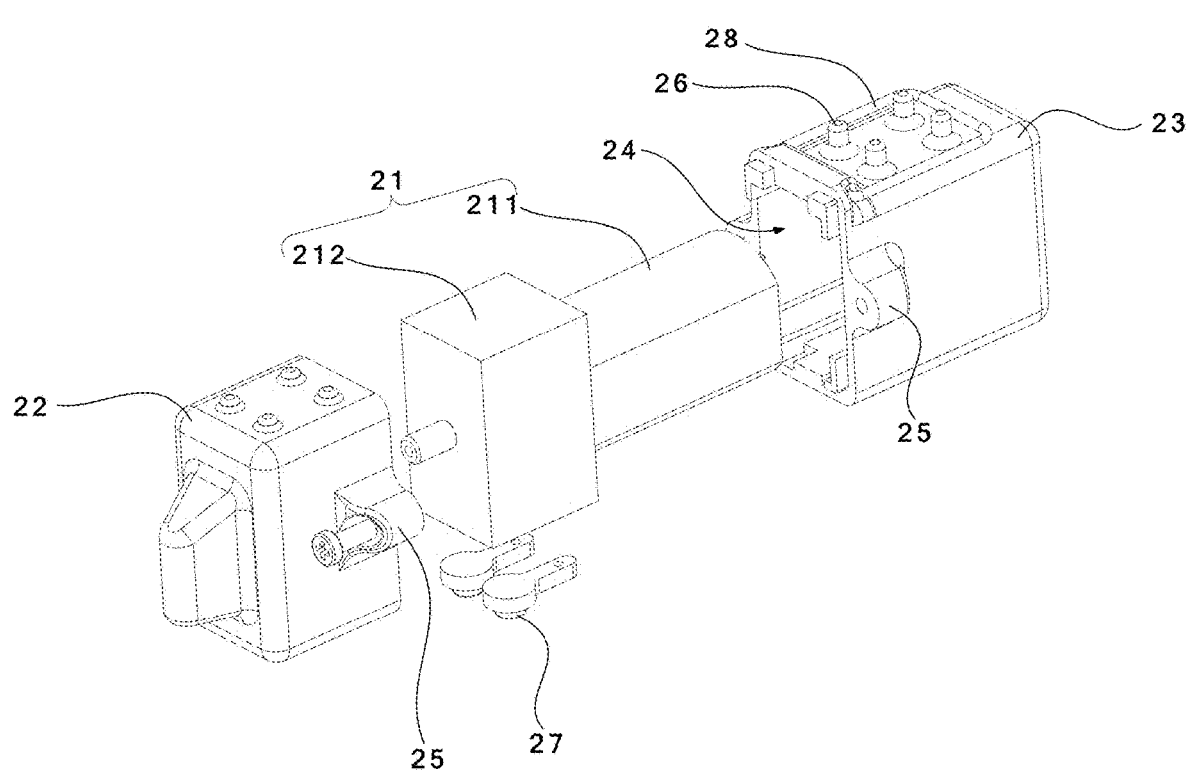
FIG. 6 is a schematic diagram of an exploded structure of an air pump body from one angle.

Further, as shown in FIGS. 4 and 6, fastening bosses 25 are protruded from opposite sides of the second housing 22 and the third housing 23, and the fastening bosses 25 of the second housing 22 and the fastening bosses 25 of the third housing 23 on the same side are fixed by screws. In this embodiment, after being buckled together, the second housing 22 and the third housing 23 are aligned and positioned by the fastening bosses 25 located on opposite sides, and screws pass through the second housing 22 and the third housing 23 for fixation, which ensures a stable connection state of the first housing 11 during long-term use. This structure facilitates disassembly and maintenance while maintaining the long-term stable operation of the air pump assembly 21, which avoids vibration transmission or noise increase caused by loosening of the first housing 11, and improves structural safety and durability.

Figure 2:
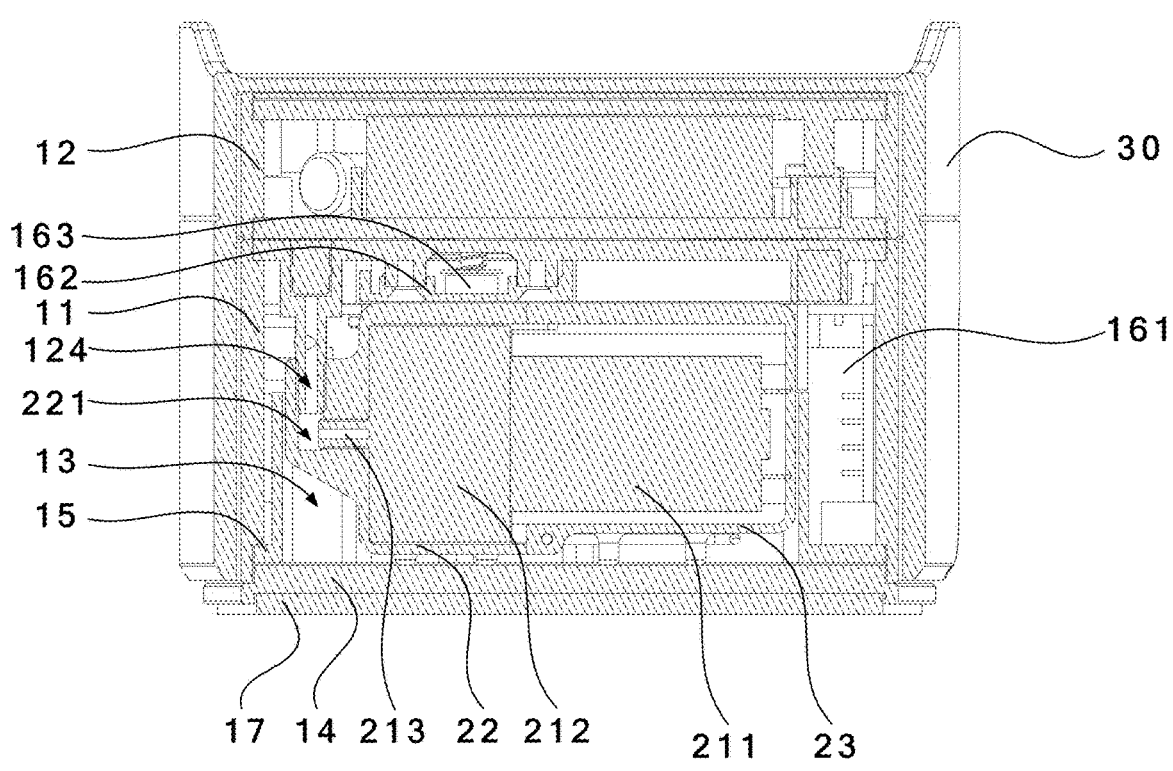
FIG. 2 is a schematic diagram of a cross-sectional structure of a vehicle-mounted aromatherapy diffuser according to the present invention from one angle.
Figure 7:
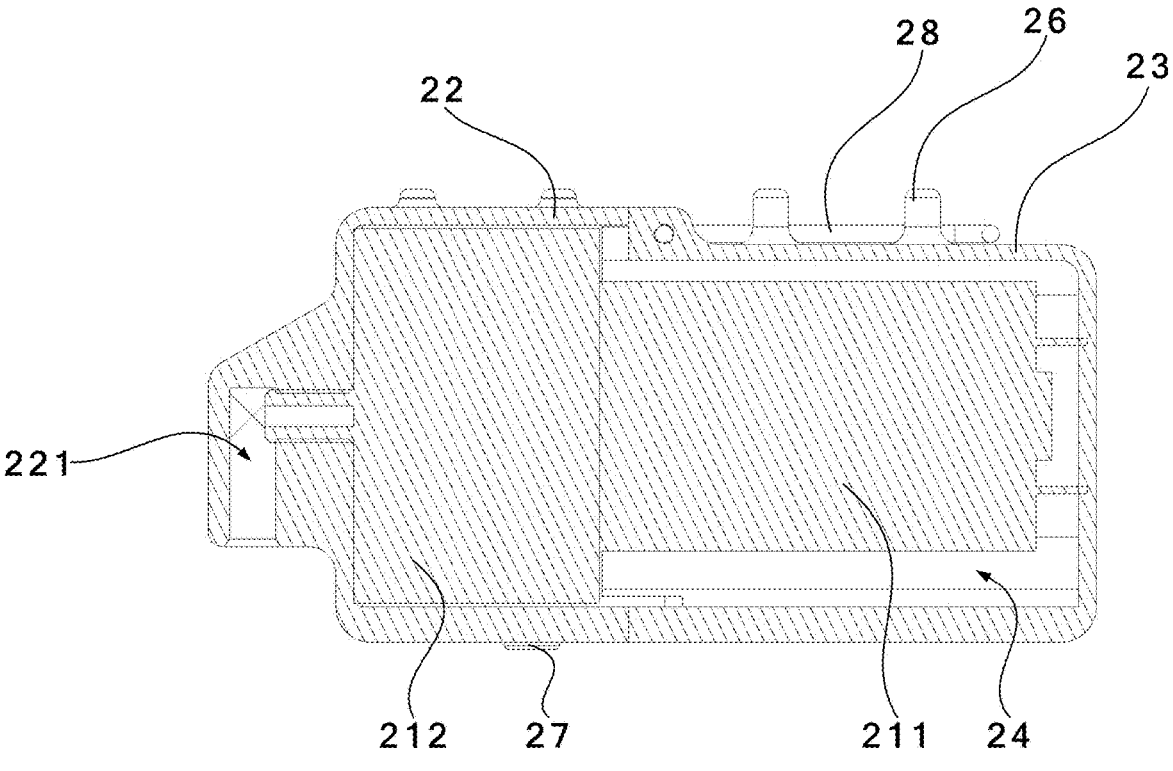
FIG. 7 is a schematic diagram of a cross-sectional structure of an air pump body from one angle.

Further, as shown in FIG. 2, FIG. 4, and FIG. 7, the second housing 22 is provided with an air guide channel 221, one end of the air guide channel 221 is communicated with the cylinder 212, and the other end of the air guide channel 221 is communicated with the atomization mechanism 12. In this embodiment, the air guide channel 221 is integrated on the second housing 22 as a part of the air flow channel. A front end of the air guide channel 221 is butted with an air outlet 213 of the cylinder 212, and a rear end extends to an air inlet 124 of the atomization mechanism 12, so that the complexity of external pipeline connection is reduced by the closed air path structure formed inside the first housing 11. Meanwhile, the second housing 22 is made of a flexible material, so that the tightness of the air path is further improved when the second housing is connected to the air path structure. Therefore, this design simplifies the air path connection process, improves the airtightness of airflow transmission and the compactness of the overall structure, and helps to improve atomization efficiency and product integration.

Figure 3:
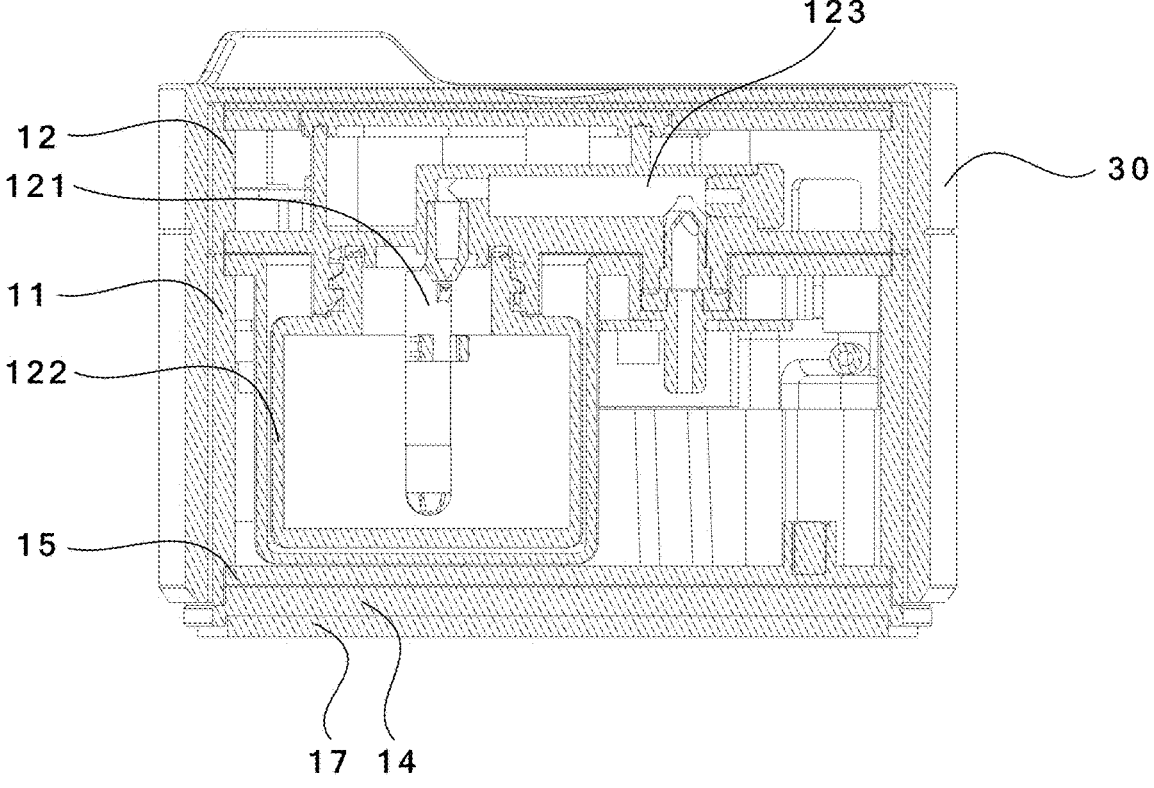
FIG. 3 is a schematic diagram of a cross-sectional structure of a vehicle-mounted aromatherapy diffuser according to the present invention from another angle.

Further, as shown in FIGS. 1 to 3, the aromatherapy body further includes a cover plate 14, the mounting groove 13 is provided at a bottom of the first housing 11, and the cover plate 14 is detachably mounted on the bottom of the first housing 11 and closes the mounting groove 13. In this embodiment, the mounting groove 13 is provided at the bottom of the first housing 11 as the embedding position of the air pump body 20; and the cover plate 14 is detachably mounted by a snap-fit or magnetic attraction structure to close the mounting groove 13. This design can achieve convenient disassembly and protection of the air pump body 20 without affecting the aesthetics and overall layout, prevent external dust or impurities from entering the first housing 11, and improve the stability and cleanliness of the device.

Further, as shown in FIGS. 1 to 7, a plurality of abutting protrusions 26 are protruded from one side of the second housing 22 and/or the third housing 23 facing the cover plate 14, and the abutting protrusions 26 abut against the cover plate 14. In this embodiment, the abutting protrusions 26 provided on the second housing 22 and/or the third housing 23 are configured to form partial surface contact with the cover plate 14, which not only plays a limiting role but also improves the assembly strength of the air pump body 20. This structure can effectively prevent the air pump from vibrating during operation, causing unstable contact with the cover plate 14 or generating resonance noise, thereby enhancing the vibration reduction capability and air tightness of the structure.

Further, as shown in FIGS. 1 to 3, the aromatherapy body also includes a mounting base 15, the mounting base 15 is fixed to the bottom of the first housing 11, the mounting groove 13 is formed on the mounting base 15, and the cover plate 14 is fixed to the mounting base 15 by magnetic attraction. In this embodiment, the mounting base 15, as a support structure of the mounting groove 13, is arranged at the bottom of the first housing 11 and is configured for embedding and stably supporting the air pump body 20. The cover plate 14 is connected to the mounting base 15 by magnetic attraction. A user can achieve tool-free disassembly and assembly by manual adsorption or removal, which is convenient for later maintenance and replacement of the air pump assembly 21. This structure ensures a secure connection while improving ease of use and optimizing user experience.

Further, the mounting base 15 is provided with a fixing groove 151, and the cover plate 14 is embedded in the fixing groove 151 to improve the mounting stability of the cover plate.

In addition, an anti-slip pad 17 is fixed to a bottom of the cover plate 14, and the anti-slip pad 17 is fixed to a vehicle in a gluing or clamping manner.

Further, as shown in FIGS. 1 to 7, the aromatherapy body also includes a main control module, the main control module includes a main control board 161 and a power supply seat 162 electrically connected to the main control board 161, a power supply terminal 163 is provided on the power supply seat 162, and the power supply seat 162 is mounted at a bottom of the mounting groove 13. An electric terminal 27 is provided at a bottom of the air pump body 20, and the electric terminal 27 is movably abutted with the power supply terminal 163 of the power supply seat 162. In this embodiment, the power supply seat 162 is fixed to the bottom of the mounting groove 13 and serves as an electrical energy input interface. The power supply terminal 163 is provided inside the power supply seat 162. The bottom of the air pump body 20 is provided with the electric terminal 27 opposite to the power supply terminal 163. In the mounting process, the air pump body 20 is inserted into the mounting groove 13 to automatically complete the electrical connection, and is disconnected after removal, forming a plug-in power supply structure. This solution omits complex wiring or plug-in processes, and improves ease of use and safety.

Further, as shown in FIGS. 4 to 7, the air pump body 20 further includes a movable handle 28, and the movable handle 28 is rotatably mounted on the third housing 23. In this embodiment, the movable handle 28 is mounted on an outer wall of the third housing 23 by a rotating shaft connection. When a user needs to disassemble the air pump body 20, the handle can be rotated to a vertical state for easy lifting. When not in use, the handle can be turned to a hidden state that fits a surface of the first housing 11. This structure is easy to operate without affecting the overall aesthetics, thereby enhancing the humanized design experience.

The above mentioned contents are only optional embodiments of the present invention and are not intended to limit the patent scope of the present invention, and under the invention concept of the present invention, the equivalent structural transformations made by using the contents of the specification and the drawings of the present invention, or direct/indirect applications to other related technical fields, are all included in the patent protection scope of the present invention.

The invention claimed is:

1. A vehicle-mounted aromatherapy diffuser, comprising:
an aromatherapy body, wherein the aromatherapy body comprises a first housing and an atomization mechanism, the atomization mechanism is mounted on the first housing, and the aromatherapy body is provided with a mounting groove; and
an air pump body, wherein the air pump body is arranged in the mounting groove, the air pump body comprises an air pump assembly, a second housing and a third housing, the second housing and the third housing are mutually buckled to form a mounting space, the air pump assembly is arranged in the mounting space and is communicated with the atomization mechanism, and the second housing is made of silicone or rubber.

2. The vehicle-mounted aromatherapy diffuser according to claim 1, wherein the air pump assembly comprises a motor and a cylinder fixed to the motor, the second housing is arranged to cover the cylinder, the third housing is arranged to cover the motor, and the cylinder is communicated with the atomization mechanism; and
a radial length of the cylinder is greater than a radial length of the motor.

3. The vehicle-mounted aromatherapy diffuser according to claim 2, wherein the third housing is made of a hard material.

4. The vehicle-mounted aromatherapy diffuser according to claim 2, wherein the second housing is provided with an air guide channel, one end of the air guide channel is communicated with the cylinder, the other end of the air guide channel is communicated with the atomization mechanism, a front end of the air guide channel is butted with an air outlet of the cylinder, and a rear end of the air guide channel extends to an air inlet of the atomization mechanism.

5. The vehicle-mounted aromatherapy diffuser according to claim 2, wherein the aromatherapy body further comprises a cover plate, the mounting groove is provided at a bottom of the first housing, and the cover plate is detachably mounted on the bottom of the first housing and closes the mounting groove.

6. The vehicle-mounted aromatherapy diffuser according to claim 5, wherein a plurality of abutting protrusions are protruded from one side of the second housing and/or the third housing facing the cover plate, and the abutting protrusions abut against the cover plate.

7. The vehicle-mounted aromatherapy diffuser according to claim 6, wherein the aromatherapy body further comprises a mounting base, the mounting base is fixed to the bottom of the first housing, the mounting groove is formed on the mounting base, and the cover plate is fixed to the mounting base by magnetic attraction.

8. The vehicle-mounted aromatherapy diffuser according to claim 7, wherein the mounting base is provided with a fixing groove, and the cover plate is embedded in the fixing groove.

9. The vehicle-mounted aromatherapy diffuser according to claim 8, wherein an anti-slip pad is provided at a bottom of the cover plate.

10. The vehicle-mounted aromatherapy diffuser according to claim 2, wherein the aromatherapy body further comprises a main control module, the main control module comprises a main control board and a power supply seat electrically connected to the main control board, a power supply terminal is provided on the power supply seat, and the power supply seat is mounted at a bottom of the mounting groove; and
an electric terminal is provided at a bottom of the air pump body, and the electric terminal is movably abutted with the power supply terminal of the power supply seat.

11. The vehicle-mounted aromatherapy diffuser according to claim 2, wherein the air pump body further comprises a movable handle, and the movable handle is rotatably mounted on the third housing.

12. The vehicle-mounted aromatherapy diffuser according to claim 1, wherein the third housing is made of acrylonitrile butadiene styrene (ABS) or polycarbonate (PC).

13. The vehicle-mounted aromatherapy diffuser according to claim 12, wherein fastening bosses are protruded from opposite sides of the second housing and the third housing, and the fastening bosses of the second housing and the fastening bosses of the third housing on the same side are fixed by screws.

14. The vehicle-mounted aromatherapy diffuser according to claim 1, wherein the vehicle-mounted aromatherapy diffuser further comprises a mounting sleeve, and the mounting sleeve is sleeved on the aromatherapy body.

* * * * *